United States Patent
Fried et al.

(10) Patent No.: US 10,159,839 B2
(45) Date of Patent: *Dec. 25, 2018

(54) SITE SPECIFIC DEEP BRAIN STIMULATION FOR ENHANCEMENT OF MEMORY

(71) Applicant: THE REGENTS OF THE UNIVERSITY OF CALIFORNIA, Oakland, CA (US)

(72) Inventors: Itzhak Fried, Los Angeles, CA (US); Nanthia Suthana, Los Angeles, CA (US); Barbara Knowlton, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/225,715

(22) Filed: Aug. 1, 2016

(65) Prior Publication Data
US 2017/0014630 A1 Jan. 19, 2017

Related U.S. Application Data

(63) Continuation of application No. 13/994,653, filed as application No. PCT/US2011/065648 on Dec. 16, 2011, now Pat. No. 9,403,010.
(Continued)

(51) Int. Cl.
*A61N 1/36* (2006.01)
*A61N 1/05* (2006.01)

(52) U.S. Cl.
CPC ..... *A61N 1/36082* (2013.01); *A61N 1/36092* (2013.01); *A61N 1/36139* (2013.01); *A61N 1/36157* (2013.01); *A61N 1/0534* (2013.01)

(58) Field of Classification Search
CPC .............. A61N 1/0534; A61N 1/36082; A61N 1/36092; A61N 1/36139; A61N 1/36157
See application file for complete search history.

(56) References Cited

U.S. PATENT DOCUMENTS

| | | | |
|---|---|---|---|
| 4,733,669 A * | 3/1988 | Segal | A61B 5/6886 600/465 |
| 6,955,675 B2 * | 10/2005 | Jain | A61B 18/1492 606/41 |

(Continued)

FOREIGN PATENT DOCUMENTS

| | | |
|---|---|---|
| WO | WO 2000/007494 A2 | 2/2000 |
| WO | WO 2009/129486 A2 | 10/2009 |

(Continued)

OTHER PUBLICATIONS

"Single pulse electrical stimulation of the himmpocampus is sufficient o impair human episodic memory" Lacruz et al., Neuroscince 170(2):623-32.*

(Continued)

*Primary Examiner* — Amanda Hulbert
(74) *Attorney, Agent, or Firm* — Morgan, Lewis & Bockius LLP

(57) ABSTRACT

The various embodiments described herein include methods, devices, and systems for enhancement of memory. In one aspect, a method includes: (1) implanting intracranial electrodes in a patient, wherein the electrodes are placed selectively at a specific brain site; (2) determining a threshold for eliciting an after-discharge threshold of the patient, and (3) stimulating the electrodes with current set below the after-discharge threshold while the patient is in a particular phase of sleep so as to enhance memory of the patient.

20 Claims, 8 Drawing Sheets

Related U.S. Application Data

(60) Provisional application No. 61/424,197, filed on Dec. 17, 2010, provisional application No. 61/474,747, filed on Apr. 13, 2011.

(56) References Cited

U.S. PATENT DOCUMENTS

| | | | |
|---|---|---|---|
| 7,437,196 | B2 | 10/2008 | Wyler et al. |
| 8,565,883 | B2* | 10/2013 | Lozano ............... A61K 45/06 607/35 |
| 2006/0079936 | A1 | 4/2006 | Boveja et al. |
| 2007/0067003 | A1 | 3/2007 | Sanchez et al. |
| 2007/0150025 | A1 | 6/2007 | DiLorenzo et al. |
| 2007/0161919 | A1 | 7/2007 | DiLorenzo |
| 2008/0255634 | A1 | 10/2008 | Jaax et al. |
| 2009/0248099 | A1* | 10/2009 | Assaf ............... A61N 1/0529 607/3 |
| 2009/0270944 | A1 | 10/2009 | Whitehurst et al. |
| 2011/0028859 | A1 | 2/2011 | Chian |
| 2014/0107728 | A1 | 4/2014 | Fried et al. |

FOREIGN PATENT DOCUMENTS

| | | |
|---|---|---|
| WO | WO 2009/135092 A2 | 11/2009 |
| WO | WO2010/111400 A2 | 9/2010 |
| WO | WO 2011/011554 A1 | 1/2011 |
| WO | WO 2012/083254 A2 | 6/2012 |

OTHER PUBLICATIONS

"Recall deficits produced by after discharges in the human hippocampal formation and amygdala" Halgren, Electroencephphalogr Clin Neurophysiol 61: 375-380.*

"Human Medial Temporal-Lob Stimulation Disrupts both formation and retrieval of recent memories" Halgren et al, Brain Cogn 4 287-295.*

Augustinack JC, Helmer K, Huber KE, Kakunoori S, Zöllei L, Fischl B. (2010) Direct visualization of the perforant pathway in the human brain with ex vivo diffusion tensor imaging. Front Hum Neurosci. 4:42.

Amaral, D.G. and Insausti, R. (1990) The hippocampal formation. The human nervous system, Academic Press, San Diego, 711-755.

Birdno, MJ et al, (2007) Pulse-to-Pulse Changes in the Frequency of Deep Brain Stimulation Affect Tremor and Modeled Neuronal Activity. J Neurophysiol 98:1675-1684.

Boon P, Vonck K, De H, V, Van DA, Goethals M, Goossens L, Van ZM, De ST, Dewaele I, Achten R, Wadman W, Dewaele F, Caemaert J, Van RD (2007) Deep brain stimulation in patients with refractory temporal lobe epilepsy. Epilepsia 48:1551-1560.

Braak, H., & Braak, E. (1991) Neuropathological stageing of Alzheimer-related changes. *Acta Neuropathologica*, 82, 239-259.

Buckner RL (2004) Memory and executive function in aging and AD: multiple factors that cause decline and reserve factors that compensate. Neuron 44:195-208.

Buzsáki, G. (2002) Theta oscillations in the hippocampus. Neuron 33, 325-340.

Carlson, JD et al., (2010) Deep Brain Stimulation Does Not Silence Neurons in Subthalamic Nucleus in Parkinson's Patients. J Neurophysiol 103:962-967.

Coleshill SG, Binnie CD, Morris RG, Alarcon G, van Emde BW, Velis DN, Simmons A, Polkey CE, van Veelen CW, van Rijen PC (2004) Material-specific recognition memory deficits elicited by unilateral hippocampal electrical stimulation. J Neurosci 24:1612-1616.

Davis K, Taub E, Houle S, et al. (1997) Globus pallidus stimulation activates the cortical motor system during alleviation of parkinsonian symptoms. Nat Med 3:671-674.

De Lacalle S, Lim C, Sobreviela T, Mufson EJ, Hersh LB, Saper CB. (1994) Cholinergic innervation in the human hippocampal formation including the entorhinal cortex. J Comp Neurol 345:321-344.

Duvernoy, H.M. (1998) The human hippocampus: Functional Anatomy, Vascularization, and Serial Sections with MRI, Springer, Berlin.

Ehret A, Haaf A, Jeltsch H, Heimrich B, Feuerstein TJ, Jackisch R (2001) Modulation of electrically evoked acetylcholine release in cultured rat septal neurones. J Neurochem 76:555-564.

Ekstrom A, Viskontas I, Kahana M, Jacobs J, Upchurch K, Bookheimer S, Fried I (2007) Contrasting roles of neural firing rate and local field potentials in human memory. Hippocampus 17:606-617.

Ekstrom AD, Caplan JB, Ho E, Shattuck K, Fried I, Kahana MJ (2005) Human hippocampal theta activity during virtual navigation. Hippocampus 15:881-889.

Ekstrom AD, Kahana MJ, Caplan JB, Fields TA, Isham EA, Newman EL, Fried I (2003) Cellular networks underlying human spatial navigation. Nature 425:184-188.

Ekstrom, A., Suthana, N.A., Salamon, N., Behnke, E., Bookheimer, S.Y., Fried, I. (2008) High-Resolution Depth Electrode Localization and Imaging in Patients with Pharmacologically Intractable Epilepsy. *Journal of Neurosurgery* 108, 812-5.

Engel J Jr (1993) Appendix 2: Presurgical evaluation protocols (University of California, Los Angeles), in Engel J Jr (ed): Surgical Treatment of the Epilepsies, ed 2. New York: Raven Press, pp. 743-745.

Fernández G, Brewer JB, Zhao Z, Glover GH, Gabrieli JD. (1999) Level of sustained entorhinal activity at study correlates with subsequent cued-recall performance: a functional magnetic resonance imaging study with high acquisition rate. Hippocampus. 1:35-44.

Feuerstein TJ, Seeger W (1997) Modulation of acetylcholine release in human cortical slices: possible implications for Alzheimer's disease. Pharmacol Ther 74:333-347.

Fried, Office Action, U.S. Appl. No. 13/994,653, dated Jun. 24, 2014, 4 pgs.

Fried, Final Office Action, U.S. Appl. No. 13/994,653, dated Feb. 13, 2015, 8 pgs.

Fried, Notice of Allowance, U.S. Appl. No. 13/994,653, dated Apr. 5, 2016, 5 pgs.

Fried I, Wilson CL, Maidment NT, Engel J Jr, Behnke E, Fields TA, MacDonald KA, Morrow JW, Ackerson L. (1999) Cerebral microdialysis combined with single-neuron and electroencephalographic recording in neurosurgical patients. Technical note. J Neurosurg. (4):697-705.

Fried I, Wilson CW, Zhang JX, et al (1993) Implantation of depth electrodes for EEG recording, in De Salles AAF, Goetsch SJ (eds): Stereotactic Surgery and Radiosurgery. Madison: Medical Physics Publishing, pp. 149-158.

Gilbert, T.H., McNamara, R.K., and Corcoran, M.E. (1996) Kindling of hippocampal field CA1 impairs spatial learning and retention in the Morris water maze. *Behav. Brain Res.* 82: 57-66.

Gloor P (1990) Experiential phenomena of temporal lobe epilepsy. Facts and hypotheses. Brain 113 6:1673-1694.

Halgren E, Walter RD, Cherlow DG, Crandall PH (1978) Mental phenomena evoked by electrical stimulation of the human hippocampal formation and amygdala. Brain 101:83-117.

Halgren E, Wilson CL (1985) Recall deficits produced by afterdischarges in the human hippocampal formation and amygdala. Electroencephalogr Clin Neurophysiol 61:375-380.

Halgren E, Wilson CL, Stapleton JM (1985) Human medial temporal-lobe stimulation disrupts both formation and retrieval of recent memories. Brain Cogn 4:287-295.

Hamani C, McAndrews MP, Cohn M, Oh M, Zumsteg D, Shapiro CM, Wennberg RA, Lozano AM (2008) Memory enhancement induced by hypothalamic/fornix deep brain stimulation. Ann Neurol 63:119-123.

Hannesson, D.K. and Corcoran, M.E. (2000) The mnemonic effects of kindling. Neurosci. Biobehav. Rev. 24: 725-751.

Hartley T, Maguire EA, Spiers HJ, Burgess N (2003) The well-worn route and the path less traveled: distinct neural bases of route following and wayfinding in humans. Neuron 37:877-888.

(56) References Cited

OTHER PUBLICATIONS

Johnson MD, Ojemann GA (2000) The role of the human thalamus in language and memory: evidence from electrophysiological studies. Brain Cogn 42:218-230.
Kadar E, Aldavert-Vera, L, Huguet, G, Costa-Miserachs, D, Morgado-Bernal, I, Segura-Torres, P, (2011) Intracranial self-stimulation induces expression of learning and memory-related genes in rat amygdala, Genes Brain and Behavior, 10:69-77.
Lacruz ME, Valentin A, Seoane JJ, Morris RG, Selway RP, Alarcón G. (2010) Single pulse electrical stimulation of the hippocampus is sufficient to impair human episodic memory. Neuroscience. 170(2):623-32.
Lang AE, Lozano AM. (1998) Parkinson's disease. Part II: medical pro-gress. N. Engl J Med 339:1130-1143.
Laxton AW, Tang-Wai DF, McAndrews MP, Zumsteg D, Wennberg R, Keren R, Wherrett J, Naglie G, Hamani C, Smith GS, Lozano AM. (2010) A phase I trial of deep brain stimulation of memory circuits in Alzheimer's disease. Ann Neurol. (in press).
Lewis PR, Shute CCD. (1967) The cholinergic limbic system: Projections to hippocampal formation, medial cortex, nuclei of ascending cholinergic reticular system, and the subfornical organ and supra-optic crest. Brain 90:521-540.
Lopes da Silva, F.H., Gorter, J.A., and Wadman, W.J. (1986) Kindling of the hippocampal induces spatial memory deficits in the rat. Neurosci. Lett. 63: 115-120.
Maguire EA (2001) Neuroimaging studies of autobiographical event memory. Philos Trans R Soc Lond B Biol Sci 356:1441-1451.
Mayberg HS, Lozano AM, Voon V, McNeely HE, Seminowicz D, Hamani C, Schwalb JM, Kennedy SH. (2005) Deep brain stimulation for treatment-resistant depression. Neuron 45:651-660.
Mount and Downton. (2006) Alzheimer disease: progress or profit? *Nature Medicine*. 12,780-784.
Newman EL, Caplan JB, Kirschen MP, Korolev IO, Sekuler R, Kahana MJ (2007) Learning your way around town: how virtual taxicab drivers learn to use both layout and landmark information. Cognition 104:231-253.
Nowak, K et al., (2011) Optimizing a Rodent Model of Parkinson's Disease for Exploring the Effects and Mechanisms of Deep Brain Stimulation. Parkinson's Disease, 19 pgs.
Pastalkova E, Serrano P, Pinkhasova D, Wallace E, Fenton AA, Sacktor TC (2006) Storage of spatial information by the maintenance mechanism of LTP. Science 313:1141-1144.
Pedreira, C, (2010) Responses of Human Medial Temporal Lobe Neurons Are Modulated by Stimulus Repetition. J Neurophysiol 103:97-107.
Penfield W, Perot P (1963) The Brain's Record of Auditory and Visual Experience. A Final Summary and Discussion. Brain 86:595-696.
Redolar-Ripoll D, Aldavert-Vera L, Soriano-Mas C, Segura-Torres P, Morgado-Bernal I (2002) Intracranial self-stimulation facilitates memory consolidation, but not retrieval: its effects are more effective than increased training. Behav Brain Res 129:65-75.
Robinson, G.B., McNeil, H.A., and Reed, R.D. (1993) Comparison of short- and long-lasting effects of perforant path kindling on radial maze learning. *Behav. Neurosci.* 6: 1-8.
Squire LR, Stark CE, Clark RE (2004) The medial temporal lobe. Annu Rev Neurosci 27:279-306.
Soriano-Mas C, Redolar-Ripoll D, Aldavert-Vera L, Morgado-Bernal I, Segura-Torres P (2005) Post-training intracranial self-stimulation facilitates a hippocampus-dependent task. Behav Brain Res 160:141-147.
Suthana NA, Ekstrom AD, Moshirvaziri S, Knowlton B, Bookheimer SY. (2009) Human hippocampal CA1 involvement during allocentric encoding of spatial information. Journal of Neuroscience 29:10512-9.
The Regents of the University of California, Decision to Grant a European Patent, EP11848517.6, dated Apr. 1, 2016, 1 pg.
The Regents of the University of California et al., International Search Report and Written Opinion, PCTUS2011/065648, dated Aug. 30, 2012, 8 pgs.
The Regents of the University of California et al., International Preliminary Report on Patentability, PCTUS2011/065648, dated Jun. 18, 2013, 5 pgs.
The Regentsof the University of California, Office Action, IL226969, dated Aug. 29, 2016, 5 pgs.
Toda H, Hamani C, Fawcett AP, Hutchison WD, Lozano AM (2008) The regulation of adult rodent hippocampal neurogenesis by deep brain stimulation. J Neurosurg 108:132-138.
Tuszynski MH, Thal L, Pay M, Salmon DP, Hs U, Bakay R, Patel P, Blesch A, Vahlsing HL, Ho G, Tong G, Potkin SG, Fallon J, Hansen L, Mufson EJ, Kordower JH, Gall C, Conner J (2005) A phase 1 clinical trial of nerve growth factor gene therapy for Alzheimer disease. Nat Med 11:551-555.
Vertes RP (2005) Hippocampal theta rhythm: a tag for short-term memory. Hippocampus 15:923-935.
Wechsler, D. (1997) *Wechsler Adult Intelligence Scale—Third edition (WAIS-III)*. San Antonio, TX: Psychological Corporation.
Wechsler D (2005) *Wechsler Memory Scale—Fourth edition*. Revised. New York, Psychological Corp/Harcourt Brace Jovanovich.
Williams JM, Givens B (2003) Stimulation-induced reset of hippocampal theta in the freely performing rat. Hippocampus 13:109-116.
Woods, S. P. Delis, D.C., Kramer, J.H., Kaplan, E., & Ober, B.A., Scott, J.C., Holdnack, J.A. (2006) California Verbal Learning Test: Second Edition. Test—retest reliability, practice effects, and reliable change indices for the standard and alternate forms. Archives of Clinical Neuropsychology 21:413-420.
Vas, C.J. et al. (2001) Alzheimer's Disease: The Brain Killer World Health Organization.
Vignai JP, Maillard L, McGonigal A, Chauvel P (2007) The dreamy state: hallucinations of autobiographic memory evoked by temporal lobe stimulations and seizures. Brain 130:88-99.
Yassa MA, Muftuler LT, Stark CE. (2010) Ultrahigh-resolution microstructural diffusion tensor imaging reveals perforant path degradation in aged humans in vivo. Proc Natl Acad Sci U S A.;107(28):12687-91.
Zeineh MM, Engel SA, Thompson P M, Bookheimer SY (2003) Dynamics of the hippocampus during encoding and retrieval of face-name pairs. Science 299:577-580.
The Regentsof the University of California, Notice of Allowance, CA2859648, dated Oct. 11, 2017, 1 pg.
The Regentsof the University of California, Notice of Allowance, IL226969, dated Aug. 14, 2017, 4 pgs.

\* cited by examiner

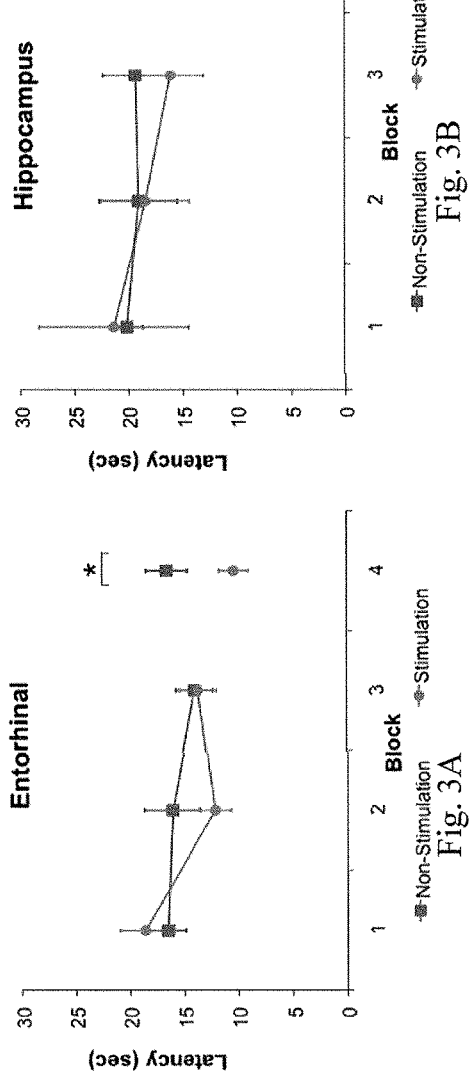
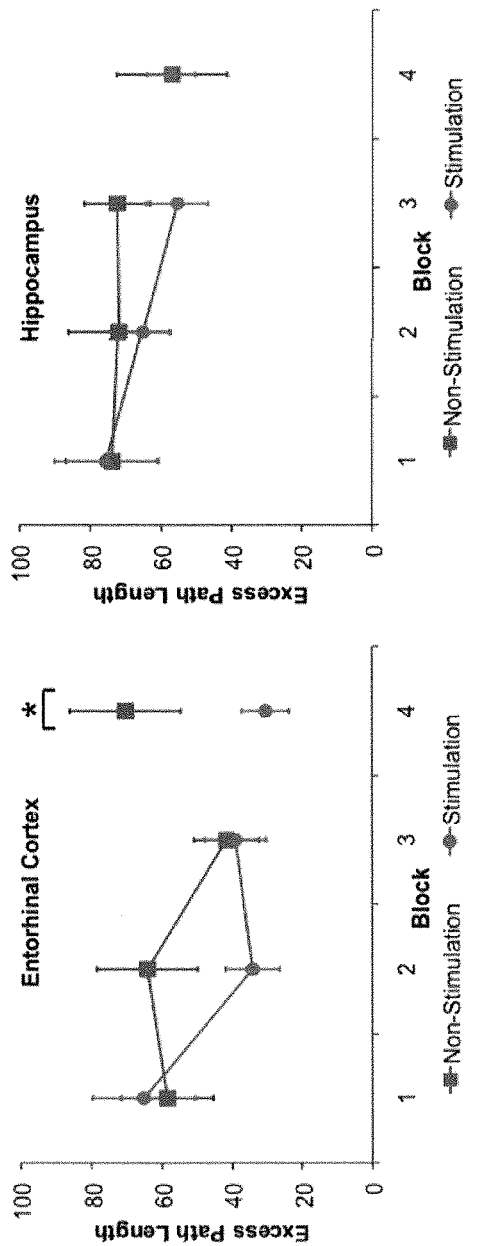

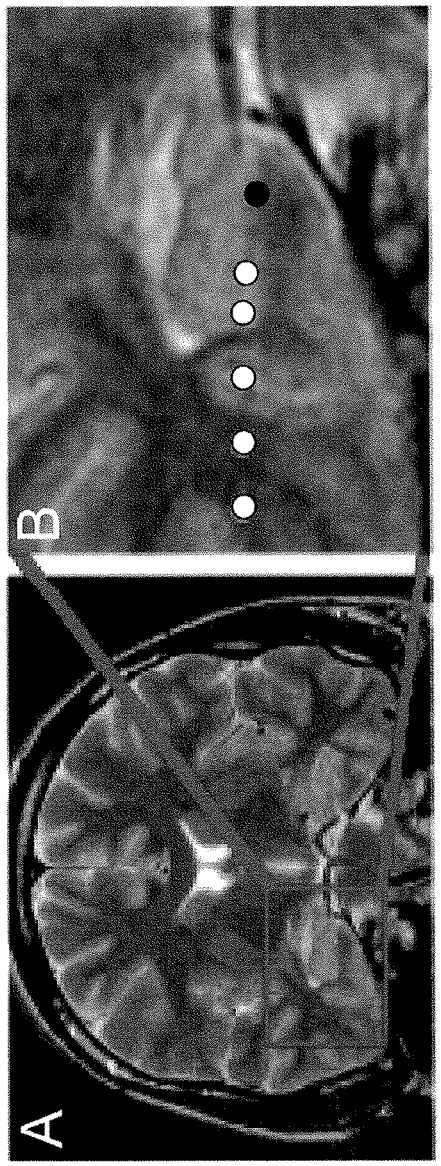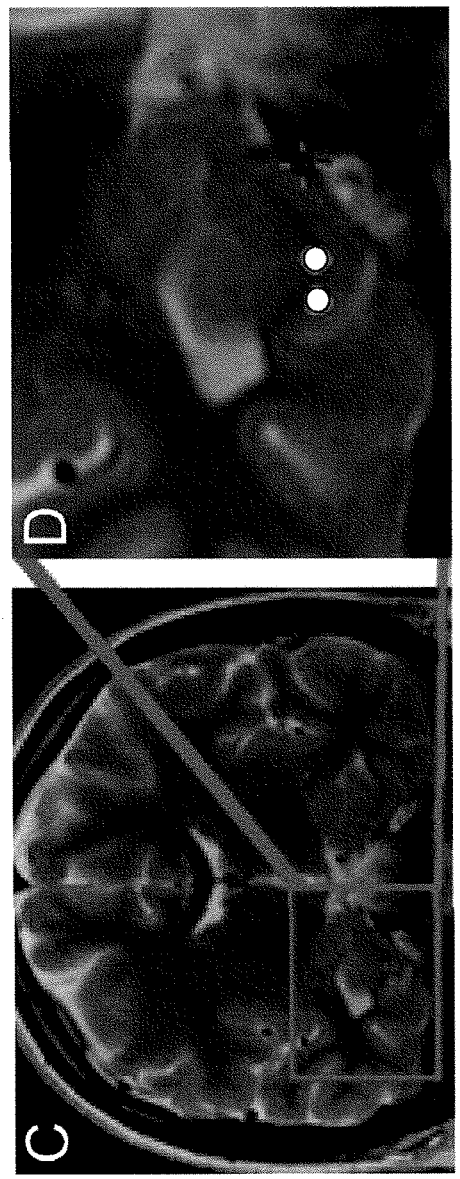

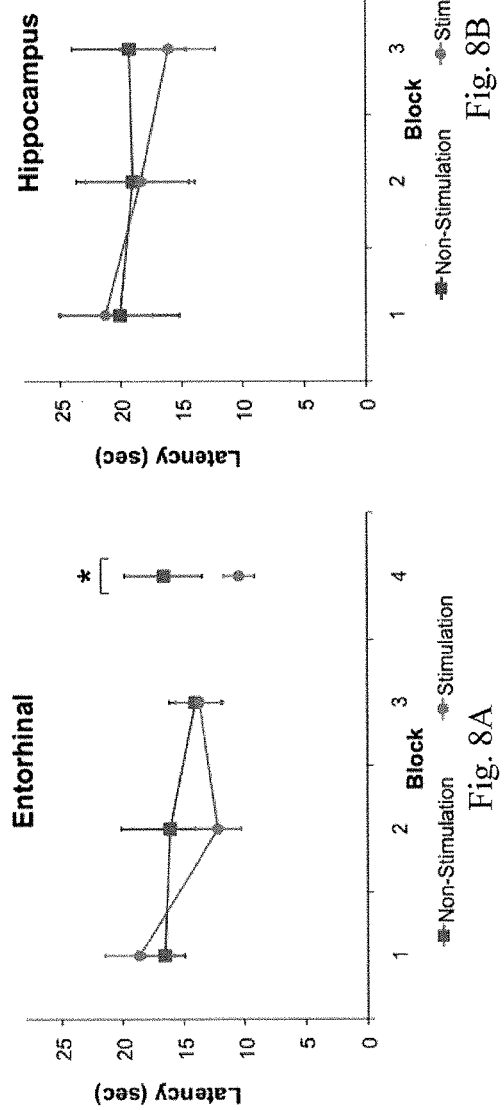
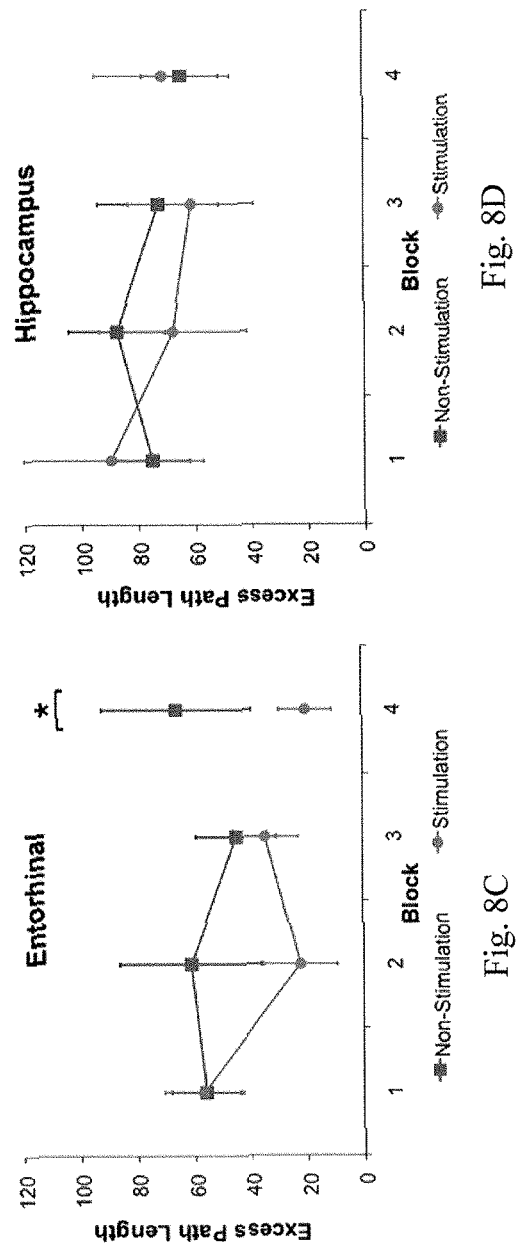
Fig. 8A
Fig. 8B
Fig. 8C
Fig. 8D

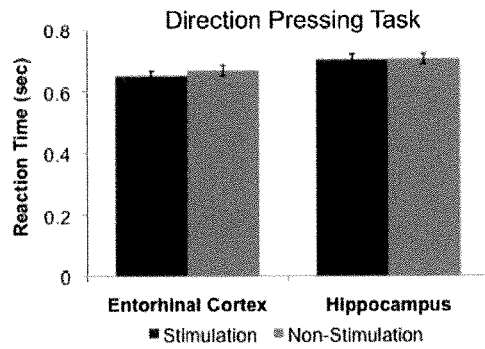 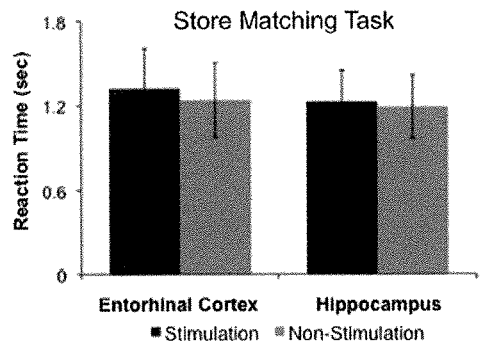
Fig. 9A  Fig. 9B
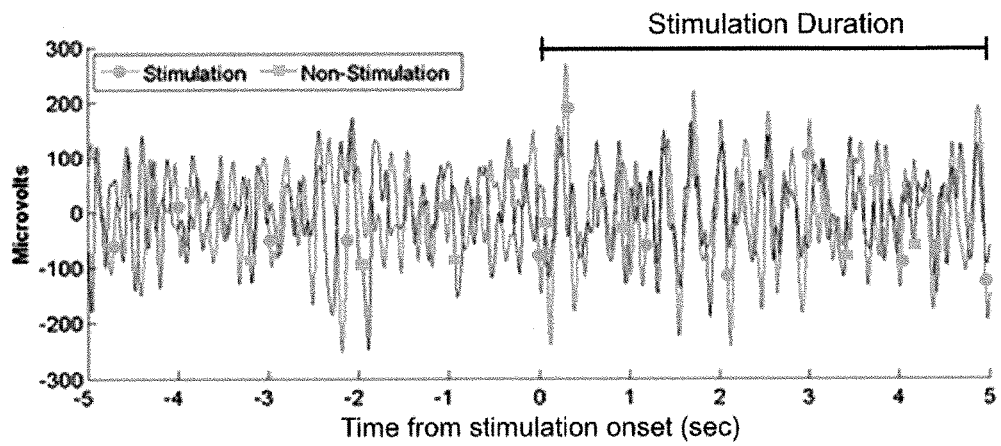
Fig. 10A
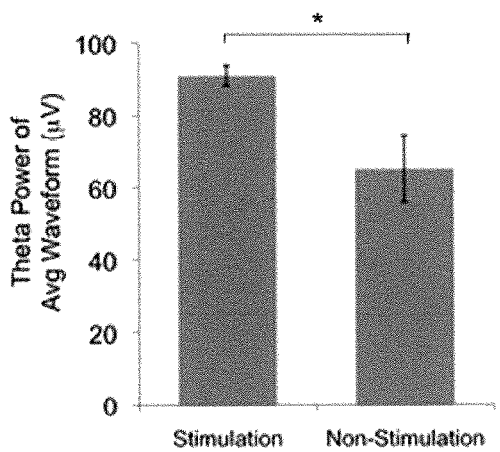 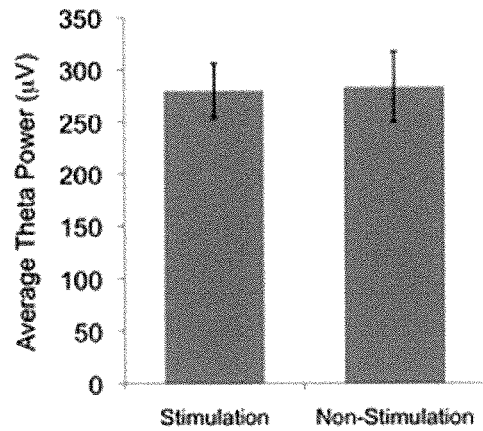
Fig. 10B  Fig. 10C

SITE SPECIFIC DEEP BRAIN STIMULATION FOR ENHANCEMENT OF MEMORY

CROSS-REFERENCES TO RELATED APPLICATIONS

This application is a continuation of U.S. patent application Ser. No. 13/994,653 filed Dec. 10, 2013, entitled "Specific Deep Brain Stimulation for Enhancement of Memory," which is a 371 application of international application PCT/US2011/065648 filed Dec. 16, 2011 entitled "Site Specific Deep Brain Stimulation for Enhancement of Memory, which claims priority to U.S. Provisional Patent Application No. 61/474,747 filed Apr. 13, 2011 and 61/424, 197 filed Dec. 17, 2010, all of which are hereby incorporated by reference in their entirety.

STATEMENT REGARDING FEDERALLY SPONSORED RESEARCH OR DEVELOPMENT

This invention was made with government support under Grant Nos. NS007449 and NS033221, awarded by the National Institutes of Health. The government has certain rights in the invention.

BACKGROUND OF THE INVENTION

This invention relates, in general, to site specific on demand deep brain stimulation for enhancement of memory.

Loss of the ability to transform experience into what can be later remembered is one of the most dreaded afflictions of the human condition. It is one of the first features of Alzheimer's disease, which affects millions of people worldwide and is an unwelcome companion of the aging process becoming an increasing burden on individuals and society as life expectancy increases. Deep brain stimulation (DBS) has emerged in recent years as a powerful technique to treat a host of neurological disorders from Parkinson's disease and dystonia to psychiatric disorders such as depression.

The medial temporal lobe of the human brain is critical for the ability to transform daily experience into lasting memories and is among the first brain centers to be affected in Alzheimer Disease with resultant changes in memory performance. The present invention is targeted at improvement of memory in humans by applying deep brain stimulation in a critical brain site at the medial temporal lobe at specific phases of information processing and with intrinsic feedback of neural signals.

BRIEF SUMMARY OF THE INVENTION

Certain aspects of Deep Brain Stimulation (DBS) in the human brain to enhance memory in accordance with the present invention is based on three principles:
1) Stimulation at a specific brain site in the medial temporal lobe: the entorhinal region, which includes the entorhinal cortex and the perforant path.
2) On demand timed stimulation (ODTS) at specific stages of information processing.
3) Real time Electroencephalographic (EEG) feedback recorded by the DBS device, including theta rhythm or other oscillatory patterns, in hippocampus or other regions, to optimize therapeutic efficacy.

Various aspects of the present invention are directed to the specific site of stimulation, the timed nature of stimulation application, which is regulated by demand and applied at specific interval of cognitive processes as an alternative to continuous stimulation, and the real time closed-loop feedback.

Potential uses of the present invention include use in patients with memory disorders such as patients with early Alzheimer Disease and other dementias, or patients with minimal cognitive impairment, or patients with memory impairment related to epilepsy or other disorders.

The detailed description below describes results with seven patients showing illustrative examples of the present invention, and that its application may result in marked enhancement of a spatial memory task of direct application to daily living.

One aspect of the present invention is directed to a method of site-specific deep brain stimulation for enhancement of memory including implanting intracranial depth electrodes, wherein the electrodes are right and/or left entorhinal-region electrodes, which may be supplemented with at least one hippocampal electrode, and stimulating the electrodes with current set below an after-discharge threshold.

Brain stimulation by the electrodes may be on-demand. The stimulating the electrodes may be continuous. The stimulating the electrodes may be intermittent. The stimulating the electrodes may be performed during a particular phase of information processing by the patient. The stimulating the electrodes may be performed while the patient is conducting a cognitive task and/or in particular stage of information processing, and/or in particular phase of sleep. The current may be regulated, charge-balanced, with biphasic rectangular pulses. The stimulating current may range from approximately 1.0 mA-2.0 mA.

Another aspect of the present invention is directed to a method of site-specific deep brain stimulation for enhancement of memory including stimulation at a specific brain site in the medial temporal lobe, stimulation (ODTS) at specific stages of information processing, and real time electroencephalographic (EEG) feedback recorded by the DBS device to optimize therapeutic efficacy.

The stimulation may be on-demand. The stimulation may be timed. The stage of information processing may be the stage of learning, and/or the stage of consolidation and/or the stage of retrieval, and/or a specific phase of sleep. The stimulation at a specific brain site may be at the entorhinal region, including the entorhinal cortex and the perforant path. The real time EEG feedback recorded may include theta rhythm in the hippocampus and/or other sites, such as in entorhinal cortex at one or more of the electrode contacts.

Still another aspect of the present invention is directed to a system for site-specific deep brain stimulation for enhancement of memory includes electrodes, wherein the electrodes are right and/or left entorhinal electrodes, and at least one hippocampal electrode, wherein the electrodes are implanted intracranially at a depth, and a stimulator for stimulating the electrodes with current set below an after-discharge threshold.

The stimulator may stimulate the electrodes and may be on-demand. The stimulator may provide current regulated, charge-balanced stimulation, with biphasic rectangular pulses. The stimulator may provide current ranges from approximately 1.0 mA-2.0 mA. One will appreciate that other ranges may be used, for example, than 2.0 mA. The stimulator may provide timed stimulation. One will also appreciate that the stimulation may be continuous or intermittent, which may or may not be regulated by demand. The stimulator may provide stimulation at a specific brain site may be at the entorhinal region, including the entorhinal cortex and the perforant path. The stimulator may include EEG recording and monitoring capabilities to regulate stimulation.

The methods and apparatuses of the present invention have other features and advantages which will be apparent from or are set forth in more detail in the accompanying drawings, which are incorporated herein, and the following Detailed Description of the Invention, which together serve to explain certain principles of the present invention.

BRIEF DESCRIPTION OF THE DRAWINGS

FIGS. 3A-D: Patients' behavioral performance on navigation tasks during unilateral stimulation and non-stimulation of the entorhinal region (A,C) and hippocampus (B,D). (A,B) Shown is the average latency and excess path length (C,D) across navigation trials (N=18) for blocks 1-4 during stimulation and non-stimulation.

FIGS. 7A-D (A) A high-resolution coronal MM of a patients' left hippocampal electrode pathway. (B) Zoomed in view of the placement of the micro-(black dot) and macro- (black circles) electrodes localized to medial temporal sub-regions. One will appreciate that various other electrode contacts may be used in accordance with the present invention. (C) A high-resolution coronal MRI of a patients' left entorhinal electrode. (D) Zoomed in view of the left entorhinal micro- and 2 distal macro-electrodes.

FIGS. 8A-D Average behavioral performance across patients on navigation tasks during unilateral stimulation and non-stimulation of the entorhinal region (A,C) and hippocampus (B,D). Shown is the average latency (A,B) and excess path length (C,D) across patients (N=6) for blocks 1-4 during stimulation and non-stimulation.

FIGS. 9A-B: (A) Reaction time during the direction-pressing and (B) store-matching control tasks with and without stimulation of entorhinal and hippocampal regions. No significant differences in reaction time were found.

FIGS. 10A-C: Hippocampal theta phase resetting with stimulation. (A) An example final average waveform with electrical stimulation of the entorhinal region. Shown are an average of 15 stimulations (circle trace) in one patient and 15 non-stimulation (square trace) trials during spatial navigation. Time of zero is stimulation or trial onset; stimulation lasted 5 seconds. (B) Hippocampal theta resetting averaged across 3 patients during entorhinal stimulation and non-stimulation navigation trials. Shown is the theta power of the final waveform average for stimulation and non-stimulation post-stimulus (5 sec each). There was a significant increase in theta resetting during stimulation vs. non-stimulation trials (*). (C) The average power of theta (microvolts [μV]) across individual trials did not differ between stimulation vs. non-stimulation periods. This shows that there was similar power of the theta rhythm during individual stimulation and non-stimulation navigation trials.

DETAILED DESCRIPTION

Figure 1:
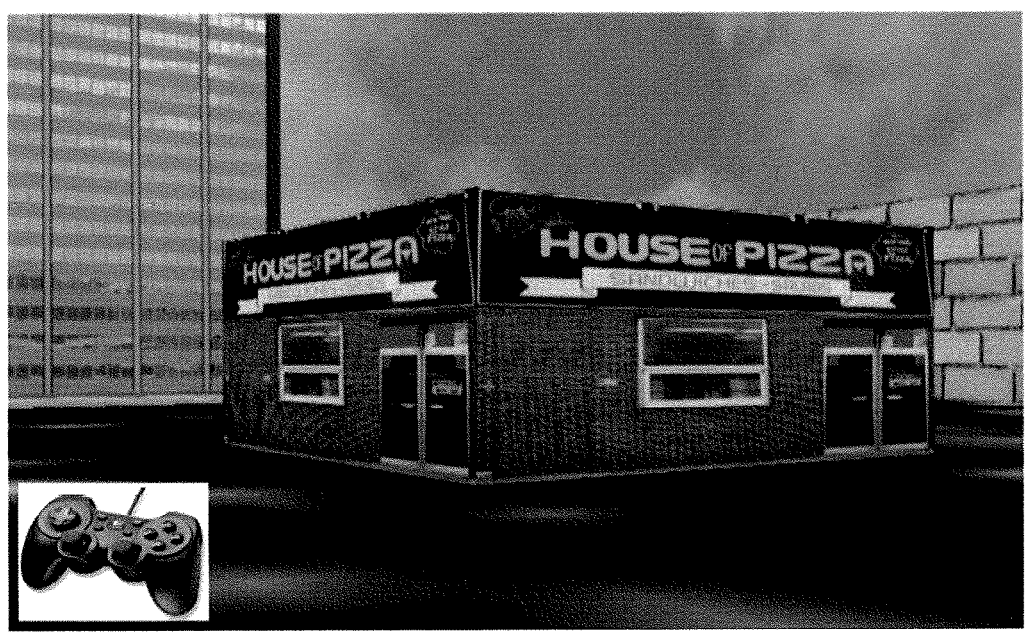
FIG. 1: An example store stimulus which patients were instructed to locate in a virtual environment using a joystick controller in a learning and memory task.

Reference will now be made in detail to various embodiments of the present invention(s), examples of which are illustrated in the accompanying drawings and described below. While the invention(s) will be described in conjunction with exemplary embodiments, it will be understood that present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

The medial temporal structures, including the hippocampus and entorhinal cortex are critical for the ability to transform daily experience into lasting memories. For example, the hippocampus is among the first brain centers to be affected in Alzheimer's Disease (AD) with resultant changes in memory performance. This study was undertaken to test the hypothesis that direct deep brain stimulation of the hippocampus or entorhinal cortex can alter memory performance.

In an exemplary study, subjects included seven neurosurgical patients implanted with intracranial depth electrodes to identify seizure-onset zones for potential curative resective surgery. Patients completed a spatial learning task where they learned various destinations within virtual environments. During half of the spatial learning trials focal electric stimulation was given below threshold required to elicit an after-discharge.

While unilateral stimulation of the hippocampus had no effect on memory performance, there was a striking enhancement of memory following unilateral stimulation of the entorhinal region, the primary source of afferents into the hippocampus. Entorhinal stimulation applied while subjects learned the location of landmarks resulted in better memory for these locations compared to those learned without stimulation. Entorhinal stimulation resulted in resetting the phase of the theta rhythm recorded in the hippocampal electroencephelagram.

Deep brain stimulation of the entorhinal region enhanced memory for spatial information when applied at the stage of learning. These results raise the possibility that deep brain stimulation of the human entorhinal region that resets the hippocampal theta wave, could be an effective method to enhance memory and may prove beneficial in conditions, such as early AD or minimal cognitive impairment (MCI), that affect learning and memory for new information. One will appreciate that stimulation applied during other stages may also enhance memory, for example, during the stage of retrieval of information, recall of information, and/or consolidation of information.

Loss of the ability to transform present experience to what can be later remembered is one of the most dreaded afflictions of the human condition. It is one of the first features of Alzheimer's Disease (AD), which affects millions of people worldwide (Mount and Downton, 2006; Vas et al., 2001) and is an unwelcome companion of the aging process becoming an increasing burden on individuals and society as life expectancy increases. Decades of research and clinical observations have established that declarative memory, the ability to remember recently experienced facts and events, depends on the hippocampus and associated structures in the medial temporal lobe (MTL), including entorhinal, perirhinal and parahippocampal cortices (for review see Squire et al., 2004). MTL structures are among the first affected in AD and other disorders affecting memory, with atrophy that is markedly disproportionate to the rest of the brain (Dickson, 2001). In AD the first affected MTL structure is the entorhinal region, the source of major input into the hippocampus (Braak & Braak, 1991; Hyman et al., 1986; Gomez-Isla et al., 1996), making declarative memory decline one of the earliest and most severe cognitive symptoms of the disease (Buckner, 2004; Bélanger et al., 1994). The MTL is also one of the earliest brain areas affected in normal aging with specific changes also affecting entorhinal-hippocampal connections within the perforant path (Burke and Barnes, 2006; Wilson et al., 2006; Yassa et al., 2010).

Deep brain stimulation (DBS) has emerged in recent years as a powerful technique to treat a host of neurologic and neuropsychiatric disorders from Parkinson's disease and dystonia, to depression, obsessive compulsion disorder and others (Lang and Lozano, 1998; Davis et al., 1997; Mayberg et al., 2005; Vidailhet et al., 2005). In some of these treatments the nature of the stimulation-induced modification of the neural circuit resulting in improvement is not completely understood and is often a matter of controversy. Clearly, the ability to apply deep brain stimulation to modify neurological functions depends on the application of stimulation at distinct and specific sites in the complex neuronal circuitry underlying these functions.

In rodents, electrical stimulation of the entorhinal perforant path has been shown to produce hippocampal long-term potentiation, acetylcholine release, and theta phase resetting, all of which are associated with improved memory function (Ehret et al., 2001; Feuerstein and Seeger, 1997; Pastalkova et al., 2006; Vertes, 2005; Williams and Givens, 2003). Whether direct stimulation of this entorhinal pathway can enhance memory in humans is unknown. To the best of our knowledge, no animal studies using perforant path stimulation during learning have shown enhancement of hippocampal dependent memory. However, electrical stimulation of targets in the rodent lateral hypothalamus during learning resulted in improved performance on tests of subsequent memory (Redolar-Ripoll et al., 2002; Soriano-Mas et al., 2005). Memory enhancement occurred early and was specific to hippocampal-dependent memory tasks (Soriano-Mas et al., 2005). Thus, stimulation seemed to act directly on specific neural circuits rather than general arousal or reward circuits.

A few studies involving direct electrical stimulation of hippocampus in humans have generally shown a disruptive effect on memory. For example, Halgren and colleagues (Halgren and Wilson, 1985; Halgren et al., 1978; Halgren et al., 1985) showed behavioral deficits including memory impairments with stimulation of hippocampus above the threshold for eliciting an after-discharge in the electroencephalogram (EEG). In another study, bilateral stimulation of the hippocampus below the after-discharge threshold did produce deficits in visual recognition memory (Halgren et al., 1985). More recently, it has been shown that stimulation of the hippocampus during encoding has negative effects on subsequent recognition memory for previously learned items (Coleshill et al., 2004; Lacruz et al., 2010). However, a recent clinical study showed that stimulation of the hippocampal inputs (the fornix/hypothalamic area) in five Alzheimer's patients resulted in increased glucose metabolism of the temporal lobes (Laxton et al., 2010), suggesting that stimulation of hippocampal afferents may have a beneficial effect.

In the present study deep brain stimulation was applied to hippocampus and entorhinal region targets while neurosurgical patients learned various locations within a novel virtual environment in order to quickly deliver passengers to particular locations. Subjects included seven patients with pharmacologically resistant epilepsy implanted with intracranial depth electrodes in order to identify seizure-onset zones for potential curative surgery. In applying deep brain stimulation to two sites in the MTL circuitry underlying declarative memory we set out to test the hypothesis that such site-specific stimulation applied at a particular phase of information processing will modify human memory.

Exemplary Methods

Patients

Seven neurosurgical patients (all right-handed, 3 female, 20-52 years old, mean age 35.4) with pharmacologically resistant epilepsy were implanted with intracranial depth electrodes for 7-10 days to determine the epileptogenic zone or area of seizure-onset for possible surgical resection. One will appreciate that the electrodes are immediately functional following the implant surgery. As such, one will appreciate that such electrodes may also be utilized to provide stimulation in chronic applications, including indefinite chronic stimulation. Patients met clinical criteria for the procedure (Engel, 1993; Fried et al., 1993) and had not undergone prior neurosurgical resection. For patient demographics, including seizure foci and neuropsychological test scores see the following tables.

Table 1 lists the patient demographics, showing the 7 patients age, gender and handedness.

TABLE 1

| Patient | Age | Gender | Handedness |
|---------|-----|--------|------------|
| 1 | 40 | M | R |
| 2 | 28 | M | R |
| 3 | 20 | F | R |
| 4 | 46 | F | R/L |
| 5 | 52 | F | R |
| 6 | 35 | M | R |
| 7 | 27 | M | R |

Table 2 lists clinical characteristics of patients. Attention (Digit Span) was calculated using the Wechsler Adult Intelligence Scale (WAIS III). Verbal and Non-verbal (visual) memory-related performance was assessed with the Wechsler Memory Scale (WMS), California Verbal Learning Test (CVLT), and the Rey-Osterrieth Complex Figure Test. Executive function was measured using the Trail Making Test (Trails B section). Neuropsychological test values are reported as percentages based on standardized scores.

TABLE 2

| Patient | WAIS VIQ | WAIS Digit Span (%) | WMS Verbal Memory (%) | CVLT Verbal Memory (%) | Rey-Osterrieth Visual Memory (%) | Trails B Executive (%) |
|---|---|---|---|---|---|---|
| 1 | 102 | 91 | 84 | 84 | 24 | 90 |
| 2 | — | 2 | 25 | 1 | 1 | 1 |
| 3 | 77 | 16 | 5 | 16 | 1 | 1 |
| 4 | 81 | 16 | 1 | 2 | 1 | 58 |
| 5 | 117 | 95 | 50 | 1 | 8 | 21 |
| 6 | 113 | 75 | 50 | 69 | 63 | 6 |
| 7 | 103 | 21 | 84 | 69 | 34 | 27 |

Table 3 includes stimulated medial temporal lobe (MTL) regions, including right and left entorhinal region (REC, LEC) and right and left hippocampal regions (RAH, LAH). Also shown are the clinically determined seizure-onset zones for each patient. CAP X indicates a region that fell with the epileptogenic zone for that patient. For each patient, MM abnormalities if any are also indicated.

TABLE 3

| Patient | REC | LEC | RAH | LAH | MRI | Seizure Focus |
|---|---|---|---|---|---|---|
| 1 | x | | | | Normal | Left Medial Temporal |
| 2 | x | | | x | Normal | Extra-Temporal |
| 3 | x | | x | | Normal | Left Medial Temporal |
| 4 | | X | x | | Left Medial Temporal | Left Medial Temporal |
| 5 | | | x | x | Normal | Supplementary Motor |
| 6 | x | | | | Normal | Left Lateral Temporal |
| 7 | | x | | x | Left Lateral Frontal | Left Lateral Frontal |

Electrode placements may be determined based on clinical criteria. Six of the seven patients had right and/or left entorhinal electrodes and all had at least one hippocampal electrode. In four of the seven patients who had both hippocampal and entorhinal electrodes implanted on the same side, EEG data was recorded and analyzed. All patients volunteered for the study by providing informed consent; the study was approved by and conformed to the Medical Institutional Review Board at UCLA.

Stimulation

Stimulation was current regulated, charge-balanced, with biphasic rectangular pulses set below the after-discharge threshold (based on pretesting; ranged from 1.0 mA-2.0 mA). Patients were blind to stimulation condition and no patient reported noticing any effect of the stimulation. Electrode contacts are stimulated through interface with a Grass C-12 stimulator, Telefactor relay box, and Stellate recording system. In this case stimulation was applied by external stimulator to demonstrate efficacy in this group of patients. One will appreciate that in chronic deep brain stimulation the stimulation may be applied by internal, specially implanted, stimulator(s). Specifically, we used 5 sec on/off trains of stimulation at 50 Hz with a 300 μsec pulse length using bipolar electrodes (0.059 cm² in surface area, 1.5 mm apart). All current delivered ranged from 0.5-2 mA (in some cases, 0.5-1.5 mA) with stimulation ranging between 2.5-10.1 μC/cm² per phase (2.5-7.6 μC/cm² per phase), well below the safe maximum used for chronic (30 μC/cm² per ph) and acute (57 μC/cm² per ph) stimulation (Agnew & McCreery, 1990; Gordon et al., 1990). The impedance measured was between 1-4 kΩ Previous human studies using stimulation parameters of up to 3.0 V, 450 μs pulse width and 130 Hz, have shown to be safe and well tolerated in patients with epilepsy with depth electrodes in the temporal lobe (Boon et al., 2007), and similar stimulation levels may be used to control seizures in epilepsy. One will appreciate that various parameters may be used in accordance with the present invention. A neurologist was present during all sessions to monitor patient at bedside and view EEG data on-line. No seizures were elicited during stimulation in the current study; similar stimulation levels have been used in clinical studies for seizure control in epilepsy (Velasco et al., 2006; Boon et al., 2007; for review see Jobst, 2009).

Behavioral Tasks

Figure 6A:
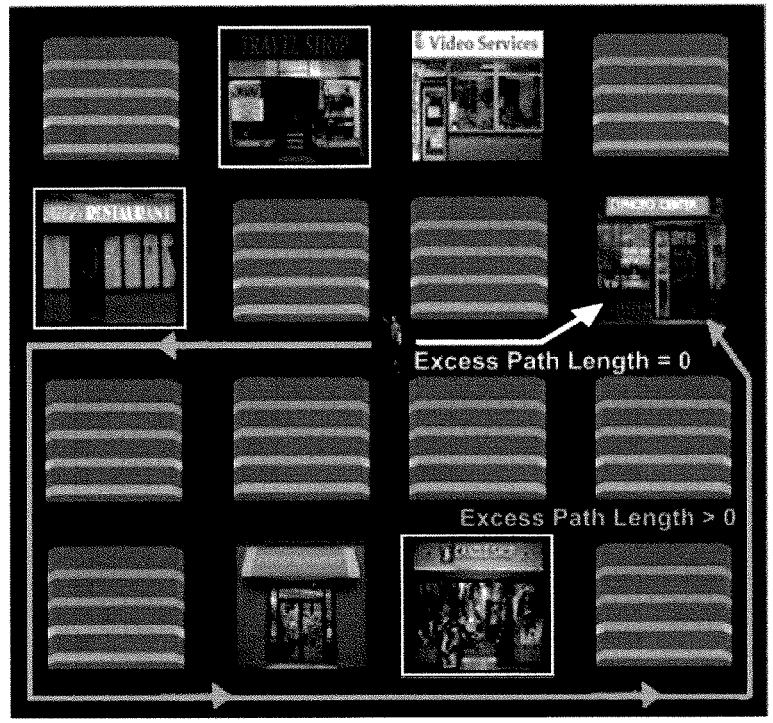
FIGS. 6A-D: (A) Top down view of an example virtual city that was used showing stores and buildings. Arrows show behavioral measurement of excess path length. Shorter excess path length (short white arrow) equals better performance. White outlined stores show example stores in which stimulation is turned on during navigation. (B) Stimuli presented during store-matching task and (C) direction-pressing control tasks. (D) Experimental paradigm consisted of alternating blocks of navigation and control (Ctl) tasks. White shows stimulated trials. During block 4 (retention) no stimulation is given on any trial.

Patients completed a spatial learning task that consisted of navigation through a virtual environment and delivery of passengers to various stores (FIG. 1A). This "yellow cab" task has been used in several studies showing MTL neuronal recruitment during navigation (Ekstrom et al., 2007; Ekstrom et al., 2003; Ekstrom et al., 2005; Suthana et al., 2009). One will appreciate that other tasks may be used including learning the names of persons, creating new associations such as face-name associations, and other types of learning and memory tasks. In order to familiarize patients with the tasks, alternate versions (with new stimuli) were given prior to testing. The experimental session consisted of alternating blocks of spatial learning and control conditions. During each spatial learning block, patients actively explored a virtual environment using a joystick by searching for passengers and delivering them to designated locations (e.g. stores). For all trials, passengers were positioned in the center of a rectangular grid-like city (FIG. 1A). Patients learned to navigate to six stores in a virtual reality environment; each store was repeated in each of the four blocks (24 total navigation trials). Starting point of each trial began from the previous trial's store location and therefore varied on each trial. Order of stores was counterbalanced within the task. For three of the stores (white boxed stores, FIG. 6A), stimulation occurred during the first 3 learning trials, and for the other 3 stores, no stimulation was given. Learning the location of stores under stimulation and no stimulation alternated, and whether learning the first store location occurred under stimulation or not was counterbalanced across patients. Each of the stores occurred equally often in the stimulation and non-stimulation condition across patients. During a "stimulation" store trial, stimulation was given throughout the entire trial in 5 sec on/off trains; time of trials varied because the trial continued until the patient located the store (Average trial time=14.76±1.84 sec). No stimulation was given during the fourth spatial block of trials (block 4) in which memory performance was assessed and compared between those locations where stimulation had been previously applied, and those locations where no stimulation had been applied.

Figure 6B:
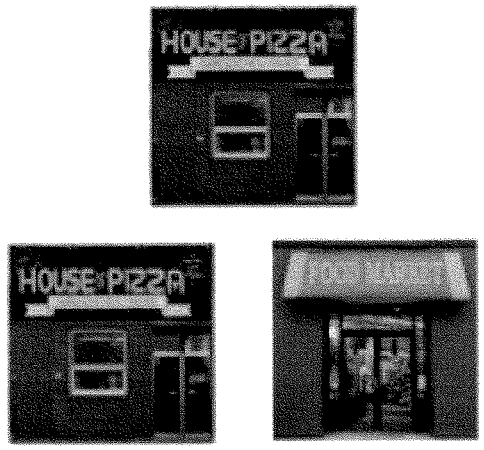
Figure 6C:
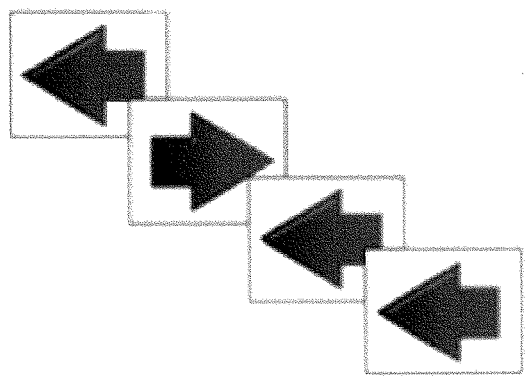
Figure 6D:
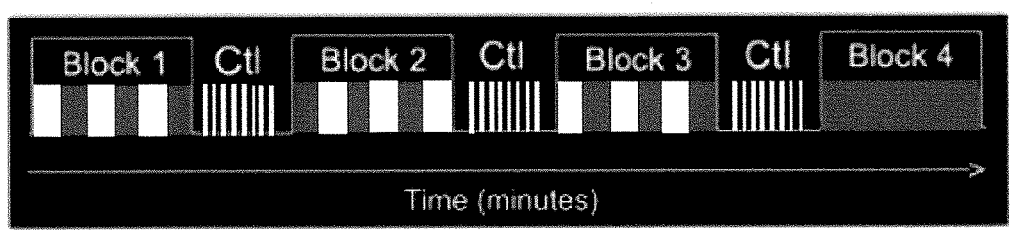

Two control tasks were interspersed within the spatial learning trials. These tasks were included to measure whether any effect of stimulation on the spatial learning task was due to improved motor or perceptual abilities. The first task was a guided navigation task in which, patients were instructed to follow the arrows on a screen using the joystick (FIG. 6C); each block lasted 1 min with stimulation during either the first or last 30 sec of the task (counterbalanced across patients). During the 30 sec stimulation periods, stimulation was given in 5 sec on/off trains. The second control task was a store-matching task where patients had to press the corresponding button in order to select one store that matched the target store presented above (FIG. 6B). Block durations were also 1 min and each trial was present for 4 seconds with a 1 sec inter-trial interval. Stimulation was given during every other store trial; stimulated trials were counterbalanced across patients.

All stimuli were presented using a Macintosh laptop computer. PyEPL (Python Experiment Program Library; http://pyepl.sourceforge.net/) was used to present virtual reality stimuli and to record navigational routes and key press reaction times. Spatial learning was quantified by first calculating the shortest path length (ideal path) from a passenger to the target store destination (Hartley et al., 2003; Newman et al., 2007). Next, the patients' actual path length was calculated. The key dependent variable in the study was the excess path length determined by subtracting the ideal path from their actual path to the store for each given trial (see FIG. 6A). The shorter the excess path length the better is the subject's performance. Reaction time performance on the control tasks was calculated using Matlab (Mathworks, Inc).

Electrode Localization

Figure 2A:
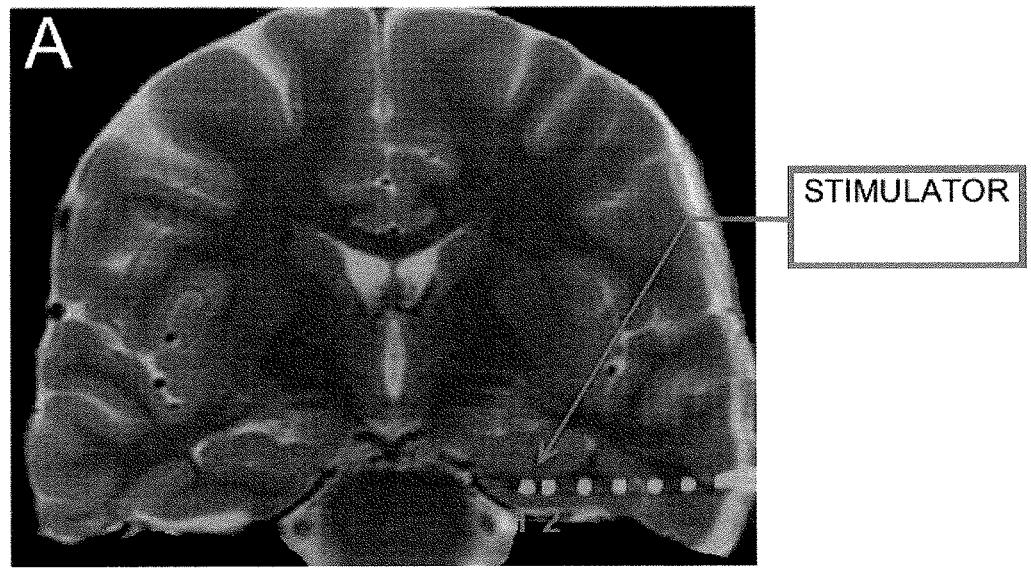
FIGS. 2A-B: (A) Two example patients' CT of electrodes registered to the high-resolution coronal MRIs showing the two distal (1=most distal) left entorhinal (A) and hippocampal (B) electrodes. For all electrodes, the two most distal macro-electrode contacts were used for stimulation.
Figure 2B:
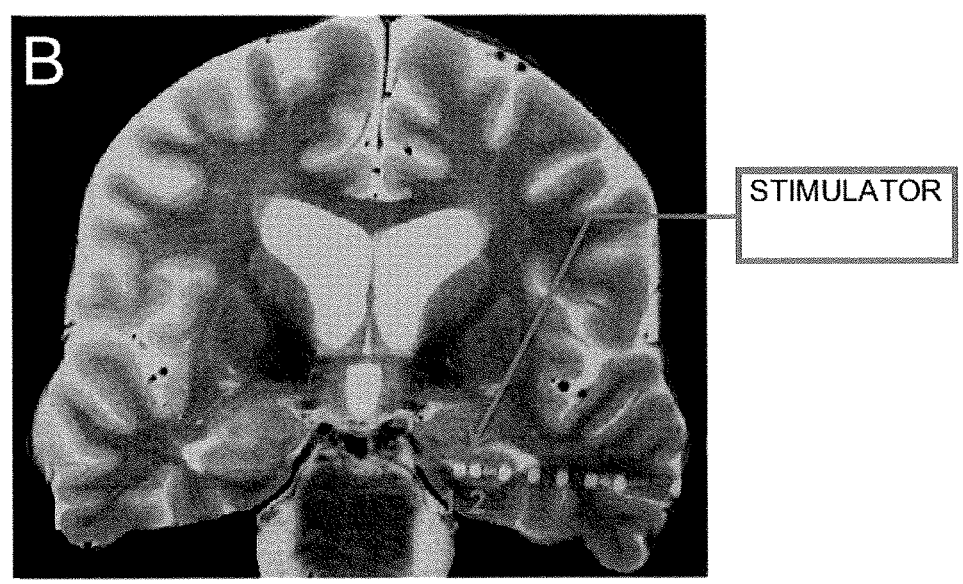

Prior to implantation with depth electrodes, patients were scanned with a Siemens Trio head-only 3 Tesla scanner. High in-plane resolution structural images with a matrix size of 512×512 (spin echo, TR=5200 ms, TE=105 ms, 19 slices, contiguous; voxel size: 0.391×0.391×3 mm) were acquired in the oblique coronal plane perpendicular to the long axis of the hippocampus. Patients also received a 3-T whole brain T1 weighted MP-RAGE GRE scan (TR=1800 msec, TE=2.93 sec, voxel size=0.9×0.9×0.8 mm) as part of depth-placement planning. Patients were then implanted with depth-electrodes by stereotactic methods for seizure monitoring as previously described (Fried et al., 1999). Following implantation with depth-electrodes, subjects received a Spiral CT scan (1 sec rotation, high-quality (HQ) mode, helical pitch 1.5, 1 mm slice collimation, and a 0.5 mm reconstruction interval to localize electrodes). CTs were registered to the high-resolution MRI and to the whole brain MRI using a 3-way registration in BrainLab stereotactic and localization software (www.brainlab.com; Gumprecht et al., 1999; Schlaier et al., 2004). Electrode contacts were registered and visualized on the high-resolution coronal MRI (FIG. 2; FIG. 7). MTL subregions were anatomically determined by boundaries that were demarcated based on atlases correlating MRI visible landmarks with underlying cellular histology (Amaral and Insausti, 1990; Duvernoy, 1998). These methods have previously been used to localize microelectrodes and investigate structural and functional dissociations within human MTL subregions (Suthana et al., 2009; Ekstrom et al. 2008, Zeineh et al., 2003). Stimulation was given using the two most distal contacts for each electrode (FIG. 2). For the hippocampus, at least one contact fell within the CA1 region of the hippocampus, whereas for the entorhinal electrodes at least one contact fell within the alvear bundle/perforant path. For all patients' electrode localizations see the following Table 4.

Table 4 includes patient electrode localizations. Region placements shown are for the two most distal macro-electrodes from the right and left anterior hippocampus (RAH and LAH), and right and left entorhinal cortex (REC and LEC). Medial Temporal Lobe (MTL) electrodes were also localized to specific gray or white matter regions within the entorhinal region and hippocampal subregions CA3 and dentate gyrus (CA3DG) or CA1.

TABLE 4

| Patient | Region | Macro | MTL Localization | Brain Matter |
|---|---|---|---|---|
| 1 | REC | 1 | Entorhinal | white |
|   |     | 2 | Entorhinal | white |
| 2 | REC | 1 | Entorhinal | white |
|   |     | 2 | Entorhinal | white |
|   | LAH | 1 | CA1 | gray |
|   |     | 2 | CA3DG | gray |
| 3 | REC | 1 | Entorhinal | white |
|   |     | 2 | Entorhinal | gray |
|   | RAH | 1 | CA1 | gray |
|   |     | 2 | ventricle | ventricle |
| 4 | LEC | 1 | Entorhinal | white |
|   |     | 2 | Entorhinal | white |
|   | RAH | 1 | CA1 | gray |
|   |     | 2 | CA1 | gray |
| 5 | RAH | 1 | CA1 | gray |
|   |     | 2 | ventricle | ventricle |
|   | LAH | 1 | CA1 | gray |
|   |     | 2 | CA1 | gray |
| 6 | REC | 1 | Entorhinal | white |
|   |     | 2 | Perirhinal | gray |
| 7 | LEC | 1 | Entorhinal | white |
|   |     | 2 | Perirhinal | gray |
|   | LAH | 1 | CA1 | gray |
|   |     | 2 | CA1 | white |

Electrophysiological Recordings and Analysis

For each patient, the threshold for eliciting an after-discharge was determined immediately prior to behavioral testing. The presence of after-discharges was determined by a clinical neurologist (Z. H or J. S). The stimulation current level for the study was set 20-25 percent below the after-discharge threshold determined for each patient. We eliminated trials from our analysis where after-discharges occurred. For all patients, no seizures had occurred within 24 hours prior to testing.

Figure 5:
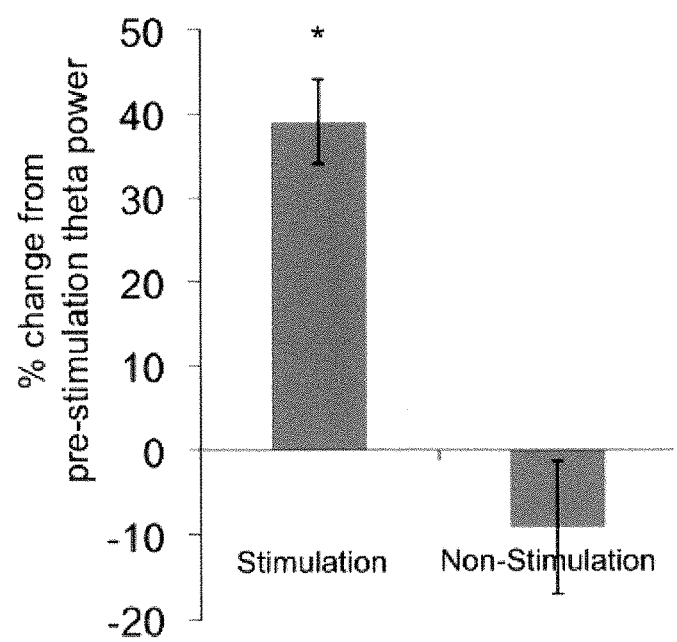
FIG. 5: Hippocampal theta resetting. Shown is the percentage (%) change in theta power of the average waveform for post- vs. pre-stimulus periods (5 sec each). Stimulation induced a 39%±5% increase in theta resetting compared to 5 sec pre-stimulation (*). There was no significant change in theta resetting during non-stimulation trials 5 sec post- compared to 5-sec pre-stimulus onset.

In the four patients with electrodes in the entorhinal and ipsilateral hippocampus, EEG data from the hippocampus were analyzed with Matlab (Mathworks, Inc). Each data record was filtered for the theta (3-8 Hz), alpha (9-14 Hz), beta (15-35 Hz), and gamma (35-100 Hz) frequencies and individually examined for artifacts and noise before being included in the EEG reset analysis. To determine if waveform resetting occurred in the hippocampus after stimulation of the entorhinal region, waveforms from the 5 seconds of each trial during and between each stimulation train were separately averaged. If phase resetting occurred during the stimulation trains, one should see greater alignment of waves and thus greater amplitude in the averaged waveform (Williams and Givens, 2003). We then calculated the percent increase in theta resetting for 5-sec post-stimulation onset compared to 5-sec pre-stimulation onset (FIG. 5). Also, we compared the power of the averaged waveforms for the stimulation and non-stimulation conditions for each of patient (FIG. 9). For non-stimulation trials, we obtained comparable averaged waveforms by averaging the waveforms for alternating 5-second periods of the non-stimulation learning trials. To insure that resetting was not due to increases in the power of each trial's rhythm, we also calculated the average power across all stimulation and non-stimulation navigation trials. We repeated the resetting analysis for each of the four frequency ranges (theta, alpha, beta, and gamma).

Statistical Analysis

In order to determine significant differences in performance between stimulation versus non-stimulation trials, we completed a 2 (condition)×3 (block) repeated measures ANOVA for excess path length in each region (entorhinal and hippocampus). For block 4, in which no stimulation was given, we did paired sample t-tests across trials ($p<0.05$, Bonferroni corrected, $N=18$ trials) to determine significant differences in excess path length for locations that had been learned under stimulation in blocks 1-3 compared to those that had been learned without stimulation. We also performed the paired sample t-tests across patients, which yielded the same results (FIG. 8; $p<0.05$, Bonferroni corrected, $N=6$ patients). In addition, for each patient we calculated the percent reduction in excess path length on block 4 for locations that had been learned during stimulation compared to those learned without stimulation. For EEG analyses, we performed paired sample t-tests ($p<0.05$; Bonferroni corrected) to compare the power of the average theta waveforms during 5-sec post-stimulation and 5-sec pre-stimulation on navigation trials (FIG. 5). We did the identical comparison for the non-stimulation navigation trials (FIG. 5). We also compared the averaged theta power across all individual stimulation and non-stimulation navigation trials (FIG. 9C) using a paired sample t-test ($p<0.05$; Bonferroni corrected). Lastly, the phase resetting analysis was repeated for each frequency range.

Exemplary Results

Behavioral Tasks

Figure 4:
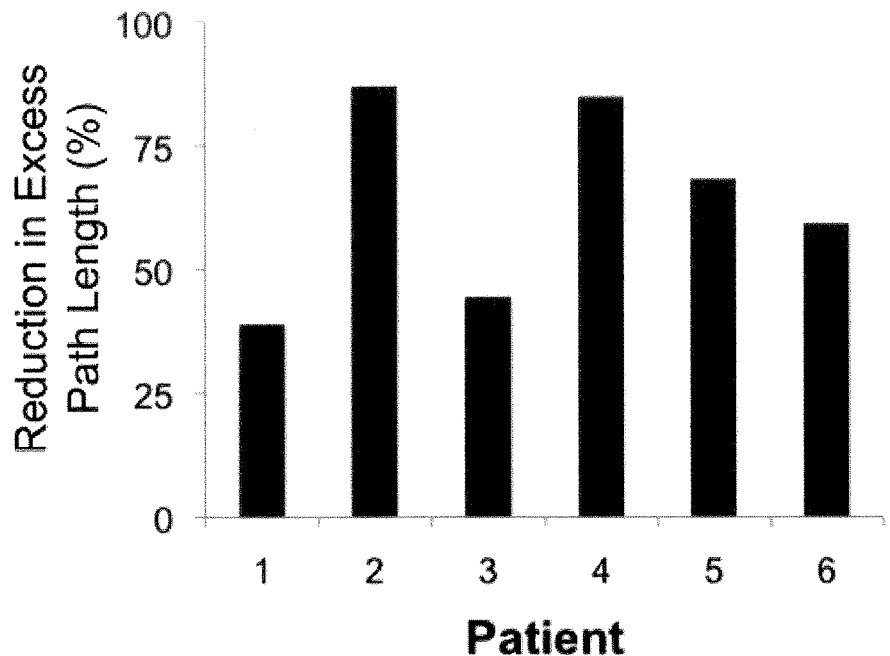
FIG. 4: For each individual patient is shown the percentage (%) reduction in excess path length during block 4 (retention) for stores during which entorhinal stimulation was given in blocks 1-3 compared to stores during which there was no stimulation. All of the six patients showed memory enhancement (shorter excess path length) for trials in which entorhinal stimulation was given below the after-discharge threshold. 100% is the maximum reduction that can occur for each patient, which would be a final excess path of zero.

FIG. 3 shows the average of patients' behavioral performance during spatial learning with unilateral stimulation of the entorhinal region ($N=18$ trials) or hippocampus ($N=18$ trials). During the spatial learning task, patients picked up passengers and delivered them to stores within a virtual city. Performance on each learning trial was measured by calculating the patients' excess path length (deviation from the shortest path to the target location). Shorter excess path length equaled better performance. Regardless of entorhinal region stimulation, there was a trend for excess path length to decrease across the first three blocks, (ANOVA Stim x block 1-3; $F(9.45)=3.145$; $p=0.056$). On the retention block (block 4), when memory for the store location was tested without stimulation, there was a significant benefit (shorter excess path length) for those locations which had been previously learned during stimulation of the entorhinal region compared to locations which had been learned without stimulation ($N=18$ trials; stim>non-stim, $t=-3.2807$; $p<0.05$, corrected). These results show that stimulation of the entorhinal region during learning results in enhancement of the performance on later recall. Strikingly, enhancement occurred in every single one of the 6 patients tested with entorhinal stimulation; average reduction in excess path length during retention with stimulation across all patients was 70% (FIG. 4). Reduced excess path indicates efficient navigation and better memory for the location of the store. Maximum improvement is 100% reduction, or a final excess path length of zero using the most efficient route. Memory enhancement effects occurred despite the wide range of neuropsychological test scores (see above Table 3). For example, Patient 2, who scored in the impaired range on standardized tests of memory and executive function, showed an 86.9% improvement for those locations learned during stimulation compared to those learned without stimulation. Even Patient 1, who performed relatively well without stimulation, was nevertheless able to improve by 38.9% to achieve optimal performance for those locations learned during stimulation. For patients 2-6, navigation to all stores learned under stimulation was more efficient than navigation to any store location learned without stimulation, demonstrating the strong reliability of the effect.

In contrast to the striking effects seen with stimulation of the entorhinal region, direct hippocampal stimulation resulted in no effect on the spatial learning task performance (stim>non-stim, $t=0.0161$; $p=n.s.$; FIG. 3B). In other words, memory performance was not enhanced, nor was it reduced, when patients navigated to locations, which had been previously learned while unilateral stimulation to the hippocampus was applied.

Neither entorhinal nor hippocampal stimulation significantly affected reaction time performance on the guided navigation control task (FIG. 8A) or the perceptual store-matching task (FIG. 8B). These results suggest that the benefits of stimulation in the spatial learning tasks were not due to general enhancement of perceptuo-motor processes involved in performing the spatial learning task.

Electrophysiological Data

In four patients who had ipsilateral entorhinal and hippocampal electrode contacts, we investigated whether stimulation of the entorhinal region affected the hippocampal theta rhythm. Supplementary FIG. 4A shows an example patient's hippocampal theta resetting (shown visually as an increase in power of the averaged waveform) after stimulation of the entorhinal region. Shown is the final average waveform of all stimulation and non-stimulation navigation trials during 5 sec pre-stimulus and during the 5 sec post-stimulation onset periods. Hippocampal theta resetting after entorhinal stimulation showed a 44.3±6.9% increase during stimulation compared to before stimulation (FIG. 5; stimulation>pre-stimulation, $t=10.72$; $p<0.05$). There was no significant difference in the percentage change of theta resetting for comparable alternating 5-second periods for non-stimulation trials (non-stimulation>pre-non-stimulation, $t=-1.3548$; $p=n.s.$). Quantification of theta resetting across all 4 patients yielded a significant increase in power of the final average waveform during stimulation vs. non-stimulation trials (FIG. 9B; stimulation>non-stimulation, $t=5.39$; $p<0.05$). Lastly, hippocampal theta resetting was not due to individual trial differences in theta power (FIG. 9C); average theta power of individual waveforms during stimulation vs. during non-stimulation trials was not significantly different. This suggests that stimulation did not merely evoke a larger theta rhythm, but rather phase-shifted an ongoing theta rhythm. We did not find significant changes during stimulation in either phase resetting (power of the average waveforms) or average power in all other frequency ranges (alpha, beta, and gamma).

Spatial navigation depends on spatial memory. Most common tasks of daily living such as finding one's care in a parking lot are dependent on the MTL. Our results show that spatial learning can be enhanced by stimulation of the entorhinal region, a specific site within the MTL and the chief gateway into the hippocampus. Indeed, stimulation of the entorhinal region while subjects were learning was associated with improved memory performance, as measured by speed and choice of route.

One will appreciate that these circuits may be modulated during other types of declarative learning and under what circumstances the consequences of such modulation is augmentative. It is possible that stimulation will also facilitate verbal, autobiographical, and associative learning and memory, which have been shown previously to rely on the MTL region (Eichenbaum et al., 2007; Squire et al., 2004; Maguire et al., 2001). Thus, a complete characterization of stimulation's effects on learning and memory will provide insights into whether electrical modulation of memory circuits could be used as a therapeutic strategy to enhance specific aspects of memory function in patients with memory disturbances.

Because of the MTL's central role in the neuroanatomy of declarative memory, it is clear how the disruption of these structures fundamentally impairs declarative memory in AD patients. It may be possible to mitigate the functional burden of the disease for a time and slow the rate of progression in memory decline by stimulating and improving function within and between these brain regions. Early results provide support for the idea of a safe, stereotactically guided surgical strategy for stimulating and enhancing neural function in early AD patients (Laxton et al., 2010; Tuszynski et al., 2005). Given that the entorhinal region is the first region affected in AD (Braak & Braak, 1991; Gomez-Isla et al., 1996), viable disease-modifying strategies would benefit from targeting the area of initial structural and functional compromise. Certainly, given evidence that electrical stimulation can enhance neurogenesis in the hippocampus (Toda et al., 2008), there is even the possibility of regeneration.

The potential effectiveness of stimulation in enhancing memory has previously been demonstrated in one human neurosurgical patient who had deep brain stimulation (DBS) electrodes implanted in the hypothalamus in close association with the fornix in an attempt to treat morbid obesity (Hamani et al., 2008). Neuropsychological testing showed enhancement of verbal recall, measured 3 months after DBS, while performance on other neuropsychological tests was unchanged. Stimulation of this fornix/hypothalamic region has also been shown to activate the medial temporal circuitry measured with EEG and positron emission tomography (PET) in 6 patients with early AD (Lacruz et al., 2010). Behavioral enhancement, was however, not clear in all patients perhaps due to the already increased rate of memory decline from the disease. Our results presented here using a within-subjects design show that stimulation of the entorhinal region, the major source of cortical afferent input into the hippocampus can strongly enhance declarative memory.

One question is whether stimulation can be effective during recall in addition to during learning. In the current study, stimulation during learning was sufficient to enhance subsequent memory when tested later without stimulation. One may appreciate that such stimulation might also enhance recall in addition to its benefits during learning.

Several animal studies have shown that stimulation of the entorhinal perforant pathway that elicits after-discharges and overt behavioral changes produces impairments in learning and memory (Lopes da Silva et al. 1986; Robinson et al. 1993; Gilbert et al. 1996; Hannesson and Corcoran, 2000). In humans, stimulation of the hippocampus above the after-discharge threshold is sufficient to impair memory (Halgren and Wilson, 1985; Halgren et 1978; Halgren et al., 1985). Other studies have shown that unilateral or bilateral stimulation below threshold for after-discharge elicitation also produced memory deficits (Lacruz et al., 2010; Halgren et al., 1985; Coleshill et al., 2004). With the stimulation parameters used here, unilateral hippocampal stimulation below threshold for after-discharges did not affect subsequent spatial memory although it is possible that bilateral hippocampal stimulation would have been disruptive.

The perforant path, consisting of major cortical afferent projections into the hippocampus (Insausti et al., 1987) has been recently visualized in humans using high-resolution diffusion tensor imaging (Yassa et al., 2010; Augustinack et al., 2010). Although we did not acquire diffusion tensor images, localization of stimulating electrodes to subjects' high-resolution structural magnetic resonance images suggest placement within the human perforant pathway. One will appreciate that it may be beneficial to specifically target the perforant path to achieve the most therapeutic efficacy.

The theta rhythm (3-8 Hz) is a large EEG potential recorded from the hippocampus in both rodents and humans (Buzaki, 2002; Winson 1978; Givens 1996; Mormann et al., 2005; Ekstrom et al., 2005; Kahana et al., 1999). Theta phase resetting, which is the phase-locking of the theta rhythm to incoming sensory stimuli, (Adey, 1967; Givens, 1996; Vinogradova et al., 1996; Brankack et al., 1998) has been suggested to enhance memory by allowing optimal encoding of novel stimuli. Stimulation of the perforant pathway has previously been shown to result in theta resetting in the rodent hippocampus (Williams and Givens 2003). In the current study, four patients who had ipsilateral hippocampal and entorhinal contacts exhibited hippocampal theta phase resetting during stimulation of the entorhinal region. In a study using functional magnetic resonance imaging (fMRI) in human subjects, information learned during increased spontaneous activity in the entorhinal cortex was subsequently remembered better (Fernandez, et al., 1999). These findings suggest that increased entorhinal input to the hippocampus can improve learning. Although further studies are needed, these preliminary results provide evidence for a possible mechanism for stimulation-induced memory enhancement in humans.

In summary, we present data here showing that stimulation of the entorhinal region during learning of a novel virtual city significantly enhanced memory performance and resulted in hippocampal theta resetting. These effects were regionally specific; stimulation of the hippocampus yielded no changes in performance. This dissociation suggests that stimulating hippocampal afferents, rather than the hippocampus itself, results in more effective learning. Furthermore, stimulation of the entorhinal region did not appear to enhance performance through improvement of general perceptuo-motor function, but rather through improved spatial learning. Overall, these results raise possibilities of a future therapeutic strategy for ameliorating memory disturbances in diseases such as early Alzheimer's disease.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

APPENDIX: REFERENCED ARTICLES

1) Amaral, D. G. & Insausti, R. (1990) The hippocampal formation. The human nervous system, Academic Press, San Diego, 711-755
2) Augustinack J C, Helmer K, Huber K E, Kakunoori S, Zöllei L, Fischl B. Direct visualization of the perforant pathway in the human brain with ex vivo diffusion tensor imaging. Front Hum Neurosci. 2010 May 28; 4:42.

3) Babb T L, Mariani E, Seidner K A, Mutafyan G, Halgren E, Wilson C L, Crandall P H (1980) A circuit for safe diagnostic electrical stimulation of the human brain. Neurol Res 2:181-197.

4) Boon P, Vonck K, De H, V, Van D A, Goethals M, Goossens L, Van Z M, De S T, Dewaele I, Achten R, Wadman W, Dewaele F, Caemaert J, Van R D (2007) Deep brain stimulation in patients with refractory temporal lobe epilepsy. Epilepsia 48:1551-1560.

5) Braak, H., & Braak, E. (1991) Neuropathological staging of Alzheimer-related changes. *Acta Neuropathologica*, 82, 239-259.

6) Buckner R L (2004) Memory and executive function in aging and A D: multiple factors that cause decline and reserve factors that compensate. Neuron 44:195-208.

7) Buzsáki, G. (2002) Theta oscillations in the hippocampus. Neuron 33, 325-340

8) Coleshill S G, Binnie C D, Morris R G, Alarcon G, van Emde B W, Velis D N, Simmons A, Polkey C E, van Veelen C W, van Rijen P C (2004) Material-specific recognition memory deficits elicited by unilateral hippocampal electrical stimulation. J Neurosci 24:1612-1616.

9) Davis K, Taub E, Houle S, et al. (1997) Globus pallidus stimulation activates the cortical motor system during alleviation of parkinsonian symptoms. Nat Med 3:671-674.

10) De Lacalle S, Lim C, Sobreviela T, Mufson E J, Hersh L B, Saper C B. 1994. Cholinergic innervation in the human hippocampal formation including the entorhinal cortex. J Comp Neurol 345:321-344.

11) Delis, D. C., Kramer, J. H., Kaplan, E., & Ober, B. A. (2000). California Verbal Learning Test: Second Edition. San Antonio, Tex.: Psychological Corporation.

12) Duvernoy, H. M. (1998) The human hippocampus: Functional Anatomy, Vascularization, and Serial Sections with Mill, Springer, Berlin.

13) Ehret A, Haaf A, Jeltsch H, Heimrich B, Feuerstein T J, Jackisch R (2001) Modulation of electrically evoked acetylcholine release in cultured rat septal neurones. J Neurochem 76:555-564.

14) Ekstrom A, Viskontas I, Kahana M, Jacobs J, Upchurch K, Bookheimer S, Fried I (2007) Contrasting roles of neural firing rate and local field potentials in human memory. Hippocampus 17:606-617.

15) Ekstrom A D, Caplan J B, Ho E, Shattuck K, Fried I, Kahana M J (2005) Human hippocampal theta activity during virtual navigation. Hippocampus 15:881-889.

16) Ekstrom A D, Kahana M J, Caplan J B, Fields T A, Isham E A, Newman E L, Fried I (2003) Cellular networks underlying human spatial navigation. Nature 425:184-188.

17) Ekstrom, A., Suthana, N. A., Salamon, N., Behnke, E., Bookheimer, S. Y., Fried, I. (2008) High-Resolution Depth Electrode Localization and Imaging in Patients with Pharmacologically Intractable Epilepsy. *Journal of Neurosurgery* 108, 812-5

18) Engel J Jr (1993) Appendix 2: presurgical evaluation protocols (University of California, Los Angeles), in Engel J Jr (ed): Surgical Treatment of the Epilepsies, ed 2. New York: Raven Press, pp 743-745

19) Fernández G, Brewer J B, Zhao Z, Glover G H, Gabrieli J D. (1999) Level of sustained entorhinal activity at study correlates with subsequent cued-recall performance: a functional magnetic resonance imaging study with high acquisition rate. Hippocampus. 1:35-44.

20) Feuerstein T J, Seeger W (1997) Modulation of acetylcholine release in human cortical slices: possible implications for Alzheimer's disease. Pharmacol Ther 74:333-347.

21) Fried I, Wilson C W, Zhang J X, et al (1993) Implantation of depth electrodes for EEG recording, in De Salles A A F, Goetsch S J (eds): Stereotactic Surgery and Radiosurgery. Madison: Medical Physics Publishing, pp 149-158

22) Fried I, Wilson C L, Maidment N T, Engel J Jr, Behnke E, Fields T A, MacDonald K A, Morrow J W, Ackerson L. (1999) Cerebral microdialysis combined with single-neuron and electroencephalographic recording in neurosurgical patients. Technical note. J Neurosurg. (4):697-705.

23) Gilbert, T. H., McNamara, R. K., and Corcoran, M. E. 1996. Kindling of hippocampal field CA1 impairs spatial learning and retention in the Morris water maze. *Behav. Brain Res.* 82: 57-66.

24) Gloor P (1990) Experiential phenomena of temporal lobe epilepsy. Facts and hypotheses. Brain 113 6:1673-1694.

25) Halgren E, Walter R D, Cherlow D G, Crandall P H (1978) Mental phenomena evoked by electrical stimulation of the human hippocampal formation and amygdala. Brain 101:83-117.

26) Halgren E, Wilson C L (1985) Recall deficits produced by afterdischarges in the human hippocampal formation and amygdala. Electroencephalogr Clin Neurophysiol 61:375-380.

27) Halgren E, Wilson C L, Stapleton J M (1985) Human medial temporal-lobe stimulation disrupts both formation and retrieval of recent memories. Brain Cogn 4:287-295.

28) Hamani C, McAndrews M P, Cohn M, Oh M, Zumsteg D, Shapiro C M, Wennberg R A, Lozano A M (2008) Memory enhancement induced by hypothalamic/fornix deep brain stimulation. Ann Neurol 63:119-123.

29) Hannesson, D. K. and Corcoran, M. E. 2000. The mnemonic effects of kindling. *Neurosci. Biobehav. Rev.* 24: 725-751.

30) Hartley T, Maguire E A, Spiers H J, Burgess N (2003) The well-worn route and the path less traveled: distinct neural bases of route following and wayfinding in humans. Neuron 37:877-888.

31) Johnson M D, Ojemann G A (2000) The role of the human thalamus in language and memory: evidence from electrophysiological studies. Brain Cogn 42:218-230.

32) Lacruz M E, Valentín A, Seoane J J, Morris R G, Selway R P, Alarcon G. (2010) Single pulse electrical stimulation of the hippocampus is sufficient to impair human episodic memory. Neuroscience. 170(2):623-32.

33) Lang A E, Lozano A M. (1998) Parkinson's disease. Part II: medical progress. N Engl J Med 339:1130-1143.

34) Laxton A W, Tang-Wai D F, McAndrews M P, Zumsteg D, Wennberg R, Keren R, Wherrett J, Naglie G, Hamani C, Smith G S, Lozano A M. (2010) A phase I trial of deep brain stimulation of memory circuits in Alzheimer's disease. Ann Neurol. (in press).

35) Lezak M D, Howieson D B, Loring D W. (2004) *Neuropsychological Assessment*. N Y Oxford University Press 36) Lewis P R, Shute C C D. (1967) The cholinergic limbic system: Projections to hippocampal formation, medial cortex, nuclei of ascending cholinergic reticular system, and the subfornical organ and supra-optic crest. Brain 90:521-540.

37) Lopes da Silva, F. H., Gorter, J. A., and Wadman, W. J. (1986) Kindling of the hippocampal induces spatial memory deficits in the rat. Neurosci. Lett. 63: 115-120
38) Maguire E A (2001) Neuroimaging studies of autobiographical event memory. Philos Trans R Soc Lond B Biol Sci 356:1441-1451.
39) Mayberg H S, Lozano A M, Voon V, McNeely H E, Seminowicz D, Hamani C, Schwalb J M, Kennedy S H. (2005) Deep brain stimulation for treatment-resistant depression. Neuron 45:651-660.
40) Meyers, J. E. & Meyers, K. R. (1995) *Rey Complex Figure Test and Recognition Trial*. Psychological Assessment Resources, Odessa, Fla., USA.
41) Mount and Downton. (2006) Alzheimer disease: progress or profit? *Nature Medicine*. 12, 780-784.
42) Newman E L, Caplan J B, Kirschen M P, Korolev I O, Sekuler R, Kahana M J (2007) Learning your way around town: how virtual taxicab drivers learn to use both layout and landmark information. Cognition 104:231-253.
43) Pastalkova E, Serrano P, Pinkhasova D, Wallace E, Fenton A A, Sacktor T C (2006) Storage of spatial information by the maintenance mechanism of LTP. Science 313:1141-1144.
44) Penfield W, PEROT P (1963) The Brain's Record of Auditory and Visual Experience. A Final Summary and Discussion. Brain 86:595-696.
45) Redolar-Ripoll D, vert-Vera L, Soriano-Mas C, Segura-Torres P, Morgado-Bernal I (2002) Intracranial self-stimulation facilitates memory consolidation, but not retrieval: its effects are more effective than increased training. Behav Brain Res 129:65-75.
46) Robinson, G. B., McNeil, H. A., and Reed, R. D. 1993. Comparison of short- and long-lasting effects of perforant path kindling on radial maze learning. *Behav. Neurosci.* 6: 1-8.
47) Squire L R, Stark C E, Clark R E (2004) The medial temporal lobe. Annu Rev Neurosci 27:279-306.
48) Soriano-Mas C, Redolar-Ripoll D, vert-Vera L, Morgado-Bernal I, Segura-Torres P (2005) Post-training intracranial self-stimulation facilitates a hippocampus-dependent task. Behav Brain Res 160:141-147.
49) Suthana N A, Ekstrom A D, Moshirvaziri S, Knowlton B, Bookheimer S Y. (2009) Human hippocampal CA1 involvement during allocentric encoding of spatial information. Journal of Neuroscience 29:10512-9.
50) Toda H, Hamani C, Fawcett A P, Hutchison W D, Lozano A M (2008) The regulation of adult rodent hippocampal neurogenesis by deep brain stimulation. J Neurosurg 108:132-138.
51) Tuszynski M R, Thal L, Pay M, Salmon D P, H S U, Bakay R, Patel P, Blesch A, Vahlsing H L, Ho G, Tong G, Potkin S G, Fallon J, Hansen L, Mufson E J, Kordower J H, Gall C, Conner J (2005) A phase 1 clinical trial of nerve growth factor gene therapy for Alzheimer disease. Nat Med 11:551-555.
52) Vertes R P (2005) Hippocampal theta rhythm: a tag for short-term memory. Hippocampus 15:923-935.
53) Wechsler, D. (1997). *Wechsler Adult Intelligence Scale—Third edition (WAIS-III)*. San Antonio, Tex.: Psychological Corporation.
54) Wechsler D (2005) Wechsler Memory Scale. Revised. New York, Psychological Corp/Harcourt Brace Jovanovich
55) Williams J M, Givens B (2003) Stimulation-induced reset of hippocampal theta in the freely performing rat. Hippocampus 13:109-116.
56) Vas, C. J. et al. Alzheimer's Disease: The Brain Killer World Health Organization. (2001).
57) Vignal J P, Maillard L, McGonigal A, Chauvel P (2007) The dreamy state: hallucinations of autobiographic memory evoked by temporal lobe stimulations and seizures. Brain 130:88-99.
58) Yassa M A, Muftuler L T, Stark C E. Ultrahigh-resolution microstructural diffusion tensor imaging reveals perforant path degradation in aged humans in vivo. Proc Natl Acad Sci USA. 2010 Jul. 13; 107(28): 12687-91.
59) Zeineh M M, Engel S A, Thompson P M, Bookheimer S Y (2003) Dynamics of the hippocampus during encoding and retrieval of face-name pairs. Science 299:577-580.

What is claimed is:
1. A method of site-specific deep brain stimulation for enhancement of memory, the method comprising:
    implanting intracranial electrodes in a patient, wherein each of the electrodes is placed selectively at a respective specific brain site in an entorhinal or hippocampal region;
    determining an individualized after-discharge threshold for eliciting an after-discharge response in the patient; and
    enhancing memory of the patient by stimulating the electrodes with current set below the individualized after-discharge threshold while the patient is in a particular phase of sleep.
2. The method of claim 1, further comprising real time electroencephalographic (EEG) feedback to optimize therapeutic efficacy of the stimulating.
3. The method of claim 2, wherein the real time EEG feedback includes evaluating theta rhythm at one or more electrode contacts.
4. The method of claim 3, wherein the real time EEG feedback includes identifying phase resetting of the theta rhythm.
5. The method of claim 1, wherein implanting the electrodes includes implanting at least one hippocampal electrode.
6. The method of claim 1, wherein at least one of the electrodes is implanted at a respective specific brain site in the entorhinal region, which includes the entorhinal cortex and/or the perforant path.
7. The method of claim 1, wherein each of the electrodes is placed selectively in white and/or gray matter of the respective specific brain site.
8. The method of claim 1, wherein the stimulating current is in the range of 1.0 mA-2.0 mA and the stimulating is on-demand.
9. The method of claim 1, wherein the patient is an Alzheimer's patient or a patient with minimal cognitive impairment (MCI) or a patient with epilepsy.
10. A method of site-specific deep brain stimulation for enhancement of memory, the method comprising:
    implanting intracranial electrodes in a patient, wherein each of the electrodes is placed selectively at a respective specific brain site in an entorhinal or hippocampal region;
    determining an individualized after-discharge threshold for eliciting an after-discharge response in the patient; and
    enhancing memory of information processing for the patient through on-demand timed stimulation of the electrodes below the individualized after-discharge threshold at a specific stage of the information processing.

11. The method of claim 10, further comprising real time electroencephalographic (EEG) feedback to optimize therapeutic efficacy.

12. The method of claim 11, wherein the real time EEG feedback includes evaluating theta rhythm at one or more electrode contacts.

13. The method of claim 12, wherein the real time EEG feedback includes identifying phase resetting of the theta rhythm.

14. The method of claim 10, wherein the stage of information processing is a stage of learning.

15. The method of claim 10, wherein the stage of information processing is a stage of retrieval of information, recall of information, and/or consolidation of information.

16. The method of claim 10, wherein the stimulation is at an entorhinal region, which includes the entorhinal cortex and the perforant path.

17. The method of claim 10, wherein each of the electrodes is placed selectively in white and/or gray matter of the respective specific brain site.

18. The method of claim 10, wherein the patient is an Alzheimer's patient or a patient with minimal cognitive impairment (MCI) or a patient with epilepsy.

19. A method of site-specific deep brain stimulation for enhancement of memory of a patient with epilepsy, the method comprising:
accessing intracranial electrodes implanted in a medial temporal lobe of the patient, wherein each electrode is selectively placed at a respective specific brain site within an entorhinal or hippocampal region;
determining an individualized after-discharge threshold for eliciting an after-discharge response in the patient; and
enhancing memory of the patient through on-demand timed stimulation of one or more contacts of the electrodes below the individualized after-discharge threshold.

20. The method of claim 19, wherein at least one electrode is selectively placed at a respective specific brain site selected for determining epileptogenic zone or area of seizure-onset for the patient and/or for treatment of the epilepsy.

* * * * *